United States Patent [19]
Schwender et al.

[11] 3,936,461
[45] Feb. 3, 1976

[54] SUBSTITUTED 4-BENZYLQUINOLINES

[75] Inventors: Charles F. Schwender, Lebanon; John Shavel, Jr., Mendham, all of N.J.

[73] Assignee: Warner-Lambert Company, Morris Plains, N.J.

[22] Filed: Oct. 17, 1974

[21] Appl. No.: 515,764

Related U.S. Application Data

[62] Division of Ser. No. 400,102, Sept. 24, 1973, abandoned.

[52] U.S. Cl... 260/289 R; 260/283 CN; 260/283 R; 260/287 R; 260/289 C; 424/258
[51] Int. Cl.² ............... C07D 215/12; C07D 215/14
[58] Field of Search ................................. 260/289 R

[56] References Cited
UNITED STATES PATENTS

| | | | |
|---|---|---|---|
| 2,519,411 | 8/1950 | Surrey et al..................... | 260/283 R |
| 2,838,514 | 6/1958 | Surrey et al..................... | 260/283 R |

*Primary Examiner*—Richard J. Gallagher
*Assistant Examiner*—D. B. Springer
*Attorney, Agent, or Firm*—Albert H. Graddis; Frank S. Chow; Anne M. Kelly

[57] ABSTRACT

The present invention relates to compounds of the formula:

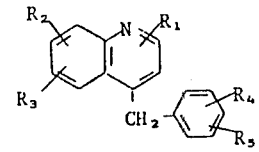

wherein $R_1$ is alkyl, $R_2$ and $R_3$ are hydrogen, halogen, alkyl, alkoxy, hydroxy, or methylenedioxy, and $R_4$ and $R_5$ are hydrogen, halogen, alkyl, alkoxy, hydroxy, or methylenedioxy and pharmaceutically acceptable salts thereof.

These compounds are useful as antianginal agents.

1 Claim, No Drawings

SUBSTITUTED 4-BENZYLQUINOLINES

This is a division, of application Serial No. 400,102 filed Sept. 24, 1973, now abandoned.

The present invention is concerned with substituted 4-benzylquinolines having the following structural formula:

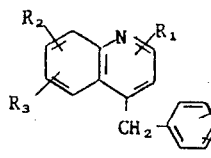

wherein $R_1$ is alkyl, $R_2$ and $R_3$ are hydrogen, halogen, alkyl, alkoxy, hydroxy, or methylenedioxy, and $R_4$ and $R_5$ are hydrogen, halogen, alkyl, alkoxy, hydroxy or methylenedioxy and pharmaceutically acceptable salts thereof.

In the above definitions for $R_1$, $R_2$, $R_3$, $R_4$ and $R_5$, the term "halogen" comprehends all four halogens, i.e., chlorine, bromine, iodine and fluorine. The term "alkyl" includes aliphatic hydrocarbons having 1 to 6 carbon atoms in the carbon chain, for example, methyl, ethyl, propyl, isopropyl, butyl, isobutyl and so on.

The compounds of this invention form acid addition salts with pharmaceutically acceptable acids such as hydrochloric, sulfuric, nitric or acetic. These salts are also included within the scope of this invention.

Among the preferred species are 6,7-dimethoxy-4-veratrylquinoline, 7-chloro-4-veratrylquinoline and 4-veratrylquinoline.

The compounds of this invention exhibit a unique mode of biological action in that they produce selective dilation of certain coronary arteries causing a redistribution of blood flow towards ischemic areas of the heart enhancing perfusion and reducing anoxia which cause anginal pains. This biological activity is demonstrated in accordance with the procedure described in J. Pharmacol. Exp. Ther., 176, 184 (1971). Only nitroglycerin and some β-adrenergic blockers have been demonstrated to similarly redistribute blood flow to ischemic areas by large coronary artery dilation. See Eur. J. Pharmacol., 16, 271 (1971). The compounds of this invention offer an advantageous treatment of angina without interference with adrenergic control of the heart or without resorting to the use of nitrates.

Existing coronary vasodilators such as dipyriadmole and chromonar dilate smaller vessels increasing coronary blood flow without redistributing flow to needed ischemic areas. In severe ischemia, dipyridamole actually induced anginal attacks in man since it diverted blood flow away from ischemic areas through its dilator action on smaller coronary vessels. See Ann. Rep. Med. Chem., 7, 69 (1972).

Experimentally, this blood flow redistribution is demonstrable in a dog by measuring changes in resistance to blood flow of larger coronary arteries (RL) relative to small vessel physical resistance to flow (RT), using the protocol described in J. Pharmacol. Exp. Ther., 176, 184 (1971).

Generally, the compounds of this invention at a dose of about 1–5 mg/kg were observed to effect a drop in the RL:RT ratio. Known coronary vasodilators such as dipyridamole and chromonar caused an increased RL:RT ratio reflecting a redistribution of blood flow away from ischemic tissues.

The compounds of this invention, particularly the preferred species, are indicated in the management of angina pectoris. A usual dose of 1–5 mg/kg by injection or orally two or three times daily is suggested to prevent anginal attack.

In order to use these compounds, they are formulated with excipients, such as lactose or water, into dosage forms, such as tablets or solutions, suitable for oral or parenteral administration, by known pharmaceutical technology.

According to the present invention, these compounds are produced by a process as illustrated in the following reaction scheme:

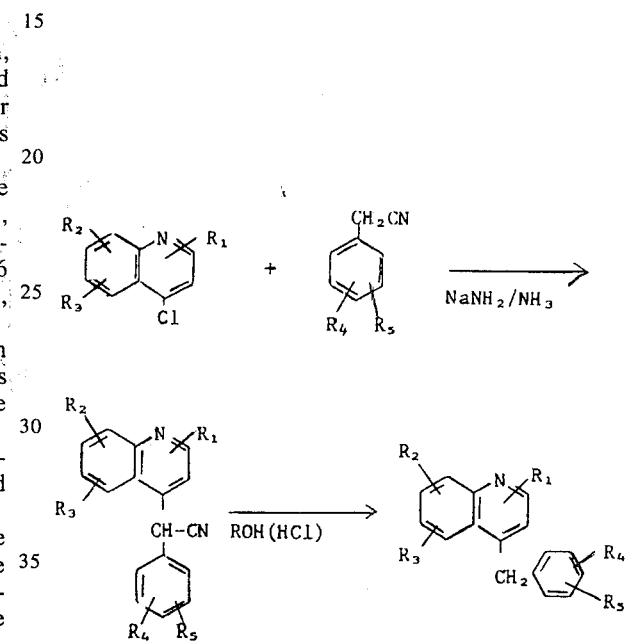

Referring now to the above reaction scheme, $R_1$, $R_2$, $R_3$-substituted chloroquinoline is condensed with a $R_4$, $R_5$-substituted phenylacetonitrile in a sodium amide-ammonia reaction mixture. The resulting $R_1$, $R_2$, $R_3$, $R_4$, $R_5$-substituted-α-quinolinyl-α-phenylacetonitrile intermediate is hydrolyzed in alcoholic hydrogen chloride to give the desired compounds of this invention.

The process of this invention utilizing sodium amide in liquid ammonia is effective in promoting the condensation of 3,4-dimethoxyphenylacetonitrile with 4-chloroquinoline and 6,7-dimethoxy-4-chloroquinoline to furnish 4-veratrylquinoline and 6,7-dimethoxy-4-veratrylquinoline, respectively, after hydrolysis. The process of U.S. Pat. No. 2,568,778 issued Sept. 25, 1951, utilizing sodium amide in benzene is ineffective in promoting these condensations.

Alternatively, treatment of a $R_1$, $R_2$, $R_3$-substituted chloroquinoline with an alkyl $R_4$, $R_5$-substitutedphenylacetate having 1 to 4 carbon atoms in the alkyl moiety of the ester group, i.e., $R_6$ is an alkyl group of 1–4 carbon atoms, in the presence of sodium hydride-dimethylformamide affords α-quinolinyl-α-phenylacetonitriles which are readily hydrolyzed by aqueous bases, such as aqueous sodium hydroxide, to the final compounds of this invention.

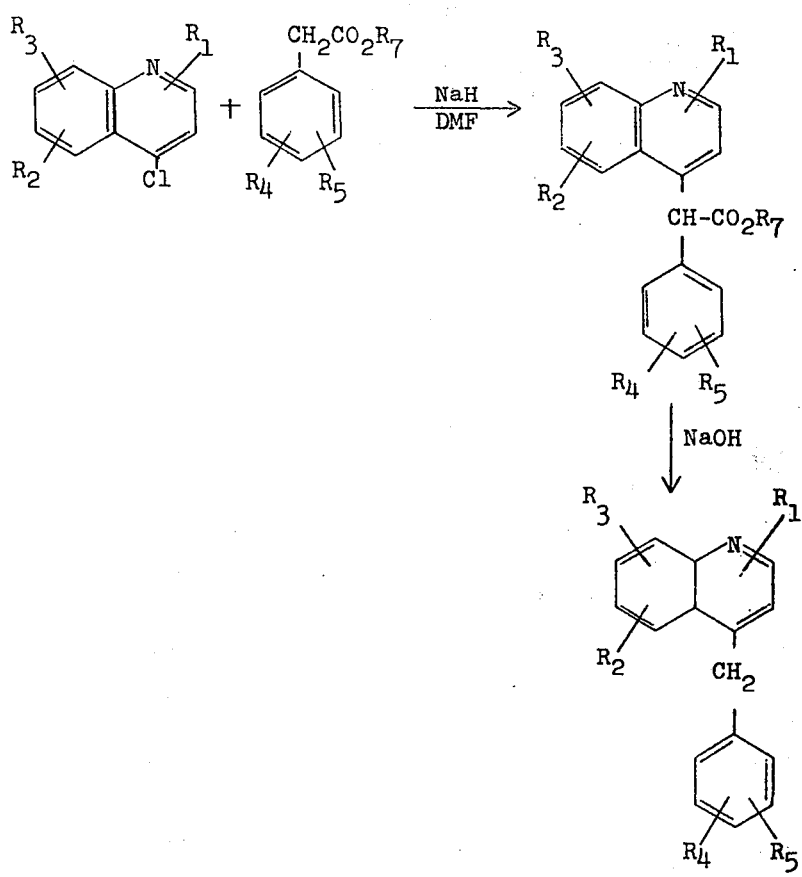

The requisite substituted 4-chloroquinolines are commercially available from chemical suppliers such as the Aldrich Chemical Company or are readily prepared by methods described by B. Riegel, J. Am. Chem. Soc., 68, 1264 (1946), E. Kaslow, J. Am. Chem. Soc., 72, 5325 (1950). The preparation of 4-chloro-6,7-methylenedioxyquinoline is described in the experimental section. The substituted phenylacetonitriles and substituted alkyl phenylacetates are available from commercial suppliers, such as the Aldrich Chemical Company.

Experimental Section

The following experimental is a general procedure for the preparation of the compounds of this invention: 4-Veratrylquinoline.

To 500 ml of liquid $NH_3$ was added 35.4 g (0.2 mol) of 3,4-dimethoxyphenylacetonitrile and 11.7 g (0.3 mol) of $NaNH_2$. The mixture was stirred for two hours, maintaining a temperature at $-25°$ to $-30°C$ by cooling in a dry ice/acetone bath. 4-Chloroquinoline (16.4 g, 0.1 mol) was added and the resulting mixture was allowed to stir at room temperature until all excess $NH_3$ had evaporated. Benzene was added to the residue and water was added slowly to destroy excess $NaNH_2$. The phases were separated and the aqueous phase was extracted with benzene. The combined benzene extracts were extracted with 9M HCl (2×150 ml). The acidic phase was washed with $Et_2O$ (500 ml), cooled and basified with concentrated $NH_4OH$. The aqueous mixture was extracted with $CHCl_3$ (500 ml). The $CHCl_3$ extract was dried with $MgSO_4$ and evaporated to give a quantitative yield of crude α-(4-quinolinyl)-α-(3,4-dimethoxyphenyl)acetonitrile intermediate.

The crude acetonitrile intermediate was dissolved in 1-butanol (500 ml). The mixture was cooled and saturated with dry HCl gas. The resultant mixture was refluxed for 48 hours and then evaporated to give a crude residue. This crude residue was dissolved in $CHCl_3$ (500 ml) and washed with 10% NaOH (250 ml) and water (500 ml) before being dried with $MgSO_4$. Evaporation of the $CHCl_3$ gave the crude product as an oil. A crystalline HCl salt was obtained from MeOH-ether; yield 25.2 g (79.8%); mp 207°–210° dec. The analytical sample was obtained by recrystallization from 2-propanol; mp 209°–211° dec.

Using the above procedures, the following compounds are obtained:

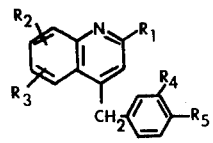

| $R_1$ | $R_2$ | $R_3$ | $R_4$ | $R_5$ | Formula | Analysis | mp°C | Solvent Recrystallization |
|---|---|---|---|---|---|---|---|---|
| H | 6-OCH$_3$ | 7-OCH$_3$ | OCH$_3$ | OCH$_3$ | $C_{20}H_{21}NO_4$ | CHN | 143–145 | 2-Propanol |
| H | 5-OCH$_3$ | 8-OCH$_3$ | OCH$_3$ | OCH$_3$ | $C_{20}H_{21}NO_4 \cdot C_2H_2O_4$ | CNH | 172–174 | 2-Propanol |
| H | H | H | CH$_3$ | CH$_3$ | $C_{18}H_{17}N \cdot HCl$ | CHNCl | 207–209dec | 2-Propanol |
| H | 7-Cl | H | OCH$_3$ | OCH$_3$ | $C_{18}H_{16}ClNO_2$ | CHNCl | 137–140 | Cyclohexane |
| H | H | H | OCH$_3$ | H | $C_{17}H_{15}NO \cdot HCl$ | CHNCl | 163–165 | 2-Propanol |
| H | H | H | OCH$_3$ | 4,5-di-OCH$_3$ | $C_{19}H_{19}NO_3 \cdot HCl$ | CHNCl | 166–168 | 2-Propanol-Ether |
| CH$_3$ | H | H | OCH$_3$ | OCH$_3$ | $C_{19}H_{19}NO_2 \cdot HCl$ | CHNCl | 243–245dec | 1-Propanol |
| H | 6-OCH$_3$ | H | H | 4-OCH$_3$ | $C_{18}H_{17}NO_2 \cdot HCl$ | CHNCl | 193–194dec | 2-Propanol |
| H | H | H | OCH$_3$ | OCH$_3$ | $C_{18}H_{17}NO_2 \cdot HCl$ | CHNCl | 209–211dec | 2-Propanol |
| H | H | H | H | OCH$_3$ | $C_{17}H_{15}NO \cdot C_7H_8SO_3$ | CHNS | 153–156 | 2-Propanol |
| H | 6,7 -O-CH$_2$-O- | | H | OCH$_3$ | $C_{18}H_{15}NO_3 \cdot HCl$ | CHNCl | 230–231dec | 1-Propanol |
| H | 6,7 -O-CH$_2$-O- | | H | H | $C_{17}H_{13}NO_2 \cdot HCl$ | CHNCl | 227–229dec | 2-Propanol |

PREPARATION OF 4-CHLORO-6,7-METHYLENEDIOXYQUINOLINE

4-Hydroxy-6,7-methylenedioxyquinoline.

A mixture of 17 g (73 mmoles) of 4-hydroxy-6,7-methylenedioxyquinoline-3-carboxylic acid, ref. 3 g, of Cu powder and 100 ml of quinoline was heated at reflux for one-half hour at an internal temperature of 235°–240°. The mixture was filtered, cooled and diluted with 250 ml of Skelly C. Filtration of the resultant precipitate yielded a light brown solid, mp 276°–279° dec. Recrystallizations from EtOH gave 9.1 g of the quinoline, mp 280°–281°C dec. ref. D. Kaminsky and R. I. Meltzer, U.S. Pat. No. 3,287,458. (Nov. 22, 1966) [Chem. abstr. 66, 65399 u (1967)].

Anal. Calcd. for $C_{10}H_7NO_3$: C, 63.49; H, 3.73; N, 7.41. Found: C, 63.40; H, 4.00; N, 7.23.

4-Chloro-6,7-methylenedioxyquinoline.

A reaction mixture containing 18.9 g (0.1 mole) of 4-hydroxy-6,7-methylenedioxyquinoline, 46 g (0.3 mole) of POCl$_3$ and 50 ml of toluene was heated at reflux for 2 hours. The volatile components of the mixture were removed by evaporation and the residue which remained was triturated with excess saturated K$_2$CO$_3$ solution. The tan solid which remained was further washed with H$_2$O and dried. The crude product was recrystallized from Skelly C to give the analytical product as crystalline platelets in good yield, mp 130°–132°.

Anal. Calcd. for $C_{10}H_6ClNO_2$: C, 57.85; H, 2.91; N, 6.75; Cl, 17.08. Found: C, 57.79; H, 2.96; H, 6.77; Cl, 17.04.

We claim:

1. A process for producing compounds of the formula:

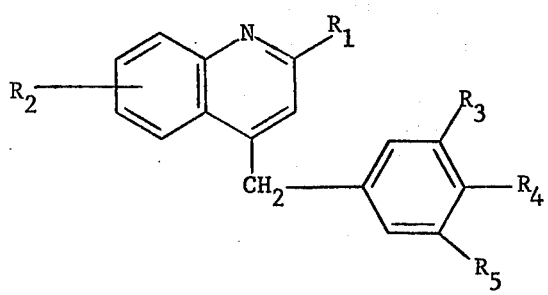

wherein $R_1$ is hydrogen or alkyl having 1 to 6 carbon atoms, $R_2$ is hydrogen, halogen, dialkoxy having 1 to 6 carbon atoms in the alkyl residues or methylendioxy, $R_3$ and $R_4$ are simultaneously alkoxy having 1 to 6 carbon atoms in the alkyl residue and $R_5$ is hydrogen or alkoxy having 1 to 6 carbon atoms in the alkyl residue which comprises (a) generating the carbanion of 1.0 molar-equivalent of a $R_3$, $R_4$, $R_5$-substituted phenylacetonitrile of the formula:

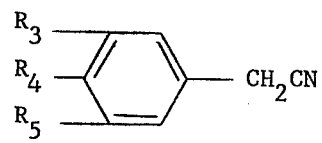

wherein $R_3$, $R_4$ and $R_5$ are as hereinbefore defined with about 1.5 molar-equivalents of sodium amide in liquid ammonia at about −25°C. to −30°C., (b) reacting the carbanion so generated with about 0.3 molar-equivalents of a $R_1$, $R_2$-substituted-4-chloroquinoline of the formula:

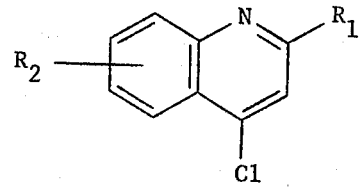

wherein $R_1$ and $R_2$ are as hereinbefore defined at about −25°C. to −30°C., (c) recovering the $R_1$, $R_2$, $R_3$, $R_4$, $R_5$-substituted-α-(4-quinolinyl)-α-phenylacetonitrile intermediate of the formula:

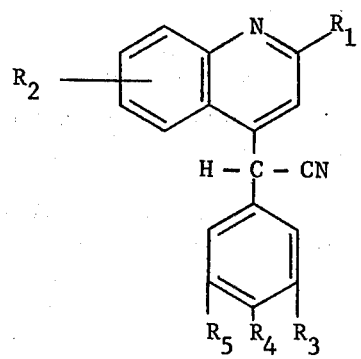

wherein $R_1$, $R_2$, $R_3$, $R_4$ and $R_5$ are as hereinbefore defined by extraction, (d) heating the s o obtained α-(4-quinolinyl)-α-phenylacetonitrile with 1-butanol saturated with hydrogen chloride under reflux and (e) recovering the product by extraction.

* * * * *